(12) United States Patent
Bauer et al.

(10) Patent No.: US 8,577,448 B2
(45) Date of Patent: Nov. 5, 2013

(54) DIFFERENTIAL APNEIC DETECTION IN AID OF DIAGNOSIS AND TREATMENT

(75) Inventors: Peter T. Bauer, WestLinn, OR (US); Patricia A. Arand, McMinnville, OR (US); Timothy K. Wheeler, Portland, OR (US)

(73) Assignee: Inovise Medical, Inc., Beaverton, OR (US)

( * ) Notice: Subject to any disclaimer, the term of this patent is extended or adjusted under 35 U.S.C. 154(b) by 1209 days.

(21) Appl. No.: 12/287,915

(22) Filed: Oct. 14, 2008

(65) Prior Publication Data
US 2010/0094148 A1 Apr. 15, 2010

(51) Int. Cl.
*A61B 5/04* (2006.01)
*A61B 5/02* (2006.01)
*A61B 7/00* (2006.01)

(52) U.S. Cl.
USPC ............ 600/513; 600/509; 600/528; 600/586

(58) Field of Classification Search
USPC .................................. 600/528, 509, 513, 586
See application file for complete search history.

(56) References Cited

U.S. PATENT DOCUMENTS

| | | | |
|---|---|---|---|
| 5,392,780 A | 2/1995 | Ogino et al. | |
| 7,039,538 B2 | 5/2006 | Baker, Jr. | |
| 7,171,269 B1 | 1/2007 | Addison et al. | |
| 7,174,203 B2 | 2/2007 | Arand et al. | |
| 7,184,817 B2 | 2/2007 | Zhu et al. | |
| 7,225,021 B1 | 5/2007 | Park et al. | |
| 7,248,923 B2 | 7/2007 | Maile et al. | |
| 7,435,221 B1 | 10/2008 | Bharmi et al. | |
| 7,559,903 B2 | 7/2009 | Moussavi et al. | |
| 7,819,814 B2* | 10/2010 | Gavriely et al. | 600/528 |
| 2004/0127792 A1 | 7/2004 | Siejko et al. | |
| 2005/0027323 A1 | 2/2005 | Mulligan et al. | |
| 2005/0080348 A1 | 4/2005 | Stahmann et al. | |
| 2005/0222515 A1* | 10/2005 | Polyshchuk et al. | 600/528 |
| 2006/0079942 A1 | 4/2006 | Deno et al. | |
| 2007/0055151 A1 | 3/2007 | Shertukde et al. | |
| 2007/0191725 A1 | 8/2007 | Nelson | |
| 2008/0021510 A1 | 1/2008 | Mi et al. | |
| 2008/0125820 A1 | 5/2008 | Stahmann et al. | |
| 2008/0177191 A1 | 7/2008 | Patangay et al. | |
| 2009/0165559 A1 | 7/2009 | Lec | |
| 2010/0331903 A1 | 12/2010 | Zhang et al. | |
| 2012/0296228 A1 | 11/2012 | Zhang et al. | |
| 2013/0030484 A1 | 1/2013 | Zhang et al. | |

OTHER PUBLICATIONS

International Search Report, Serial No. PCT/US10/055696, dated Dec. 23, 2010, 13 pages total.
USPTO Office Action, U.S. Appl. No. 12/315,165, dated Nov. 12, 2010, 9 pages total.

(Continued)

*Primary Examiner* — Mark W Bockelman
(74) *Attorney, Agent, or Firm* — Jon M. Dickinson, Esq.; Robert D. Varitz, Esq.

(57) ABSTRACT

A computer-based detection method employable with a sleeping subject for aiding in the differential-character diagnosis and treatments of apneic events includes gathering heart-sound data, including S1 data and S2 data. A combined time-frequency-intensity (TFI) analysis, of the gathered data is performed, in a continuous manner, over a selected time period. Based on the performing and the performed TFI analysis, an output is produced which is indicative of the presence and character of any detected apneic event.

3 Claims, 3 Drawing Sheets

(56) References Cited

OTHER PUBLICATIONS

USPTO Office Action, U.S. Appl. No. 11/264,328, dated May 9, 2008, 7 pages total.
USPTO Office Action, U.S. Appl. No. 11/264,328, dated Oct. 16, 2008, 8 pages total.
USPTO Office Action for U.S. Appl. No. 12/321,646 dated Jun. 17, 2011. 9pp.
USPTO Office Action for U.S. Appl. No. 12/288,712 dated Apr. 11, 2011. 5pp.
USPTO Office Action for U.S. Appl. No. 12/321,647 dated Jun. 1, 2011. 7pp.
USPTO Office Action for U.S. Appl. No. 12/321,650 dated Sep. 7, 2011. 8 pp.
USPTO Office Action for U.S. Appl. No. 12/005,555 dated Dec. 23, 2010. 7pp.

* cited by examiner

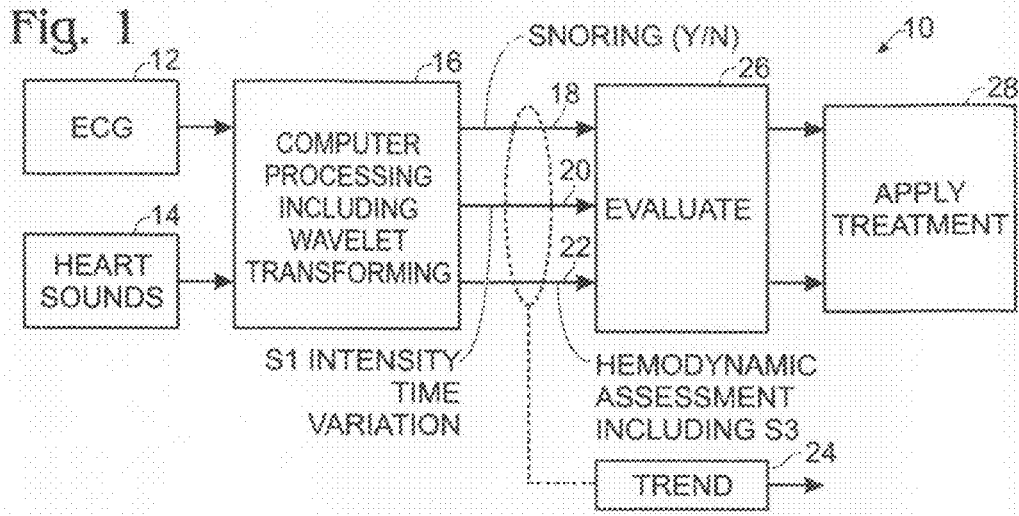
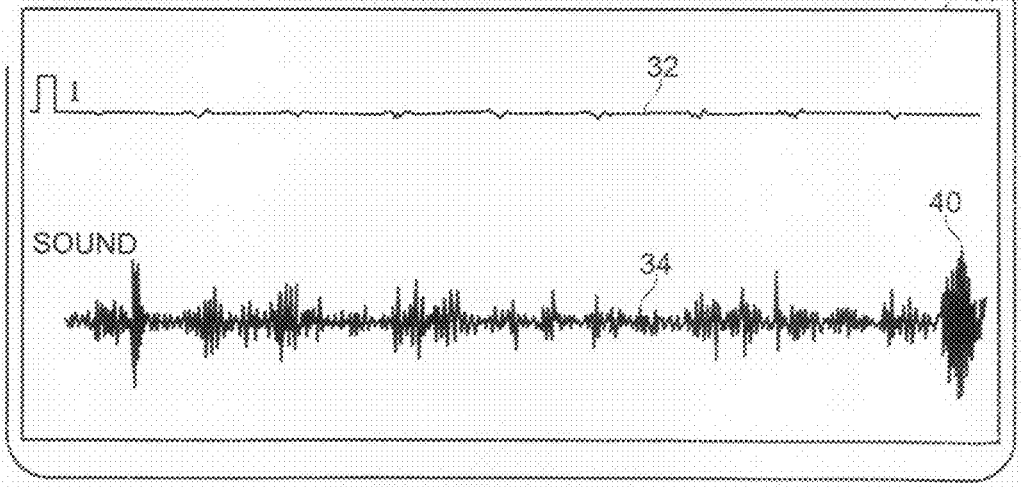

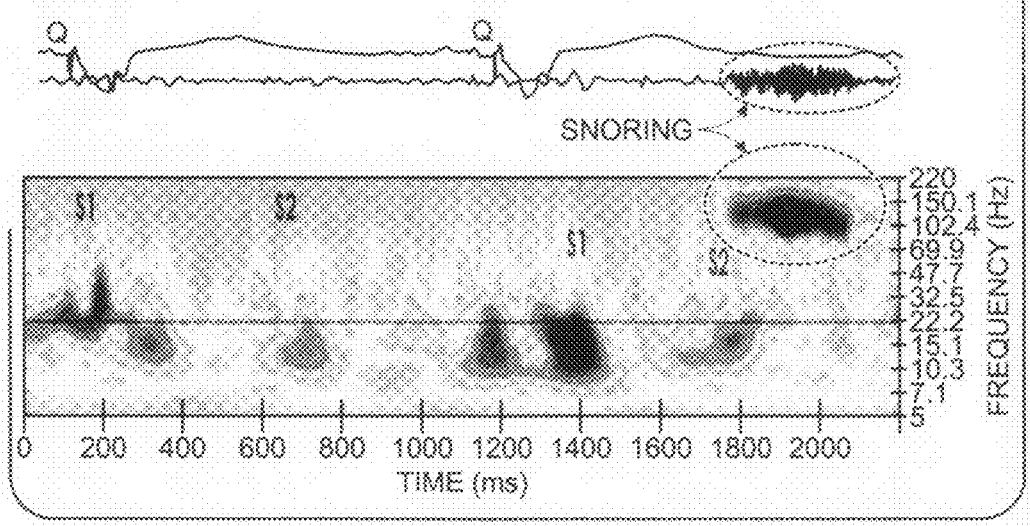
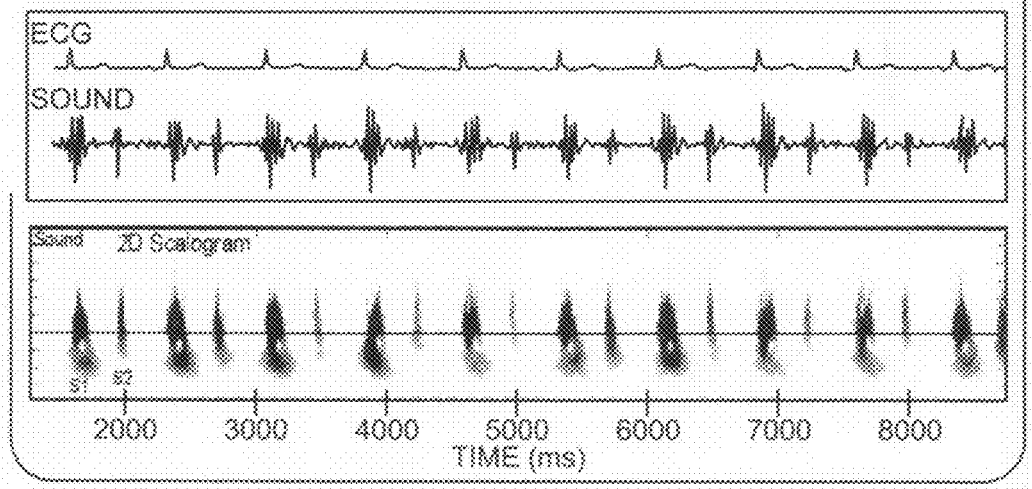

DIFFERENTIAL APNEIC DETECTION IN AID OF DIAGNOSIS AND TREATMENT

FIELD OF THE INVENTION

This invention is related to treatment for sleep apnea, and specifically to diagnosis and treatment of apneic events by monitoring ECG and heart sounds.

BACKGROUND OF THE INVENTION

Sleep apnea is a sleep disorder characterized by pauses in breathing during sleep. These episodes, called apneas, each last long enough so one or more breaths are missed, and occur repeatedly throughout sleep. There are two main forms of sleep apnea: central and obstructive. Central sleep apnea is related to a dysfunction of the autonomous nervous system, which can lead to long breathing pauses, while obstructed airway paths cause obstructive sleep apnea. The differential diagnosis of both forms of apnea is non-trivial, and multiple vital signs are recorded and analyzed to achieve high diagnostic performance. The presence and frequency of snoring episodes is one of the markers helping to diagnose obstructive sleep apnea.

SUMMARY OF THE INVENTION

The present invention involves a computer-based detection method employable with a sleeping subject for aiding in the differential-character diagnosis and treatments of apneic events includes gathering heart-sound data, including S1, S2 and S3 and/or S4 data. A combined time-frequency-intensity (TFI) analysis, of portions of the gathered data is performed, in a continuous manner, over a selected time period. Based on the performing and the performed TFI analysis, an output is produced which is indicative of the presence and character of any detected apneic event.

This summary and objectives of the invention are provided to enable quick comprehension of the nature of the invention. A more thorough understanding of the invention may be obtained by reference to the following detailed description of the preferred embodiment of the invention in connection with the drawings.

BRIEF DESCRIPTION OF THE DRAWINGS

FIG. 1 is a block diagram depicting the method of the invention.

FIG. 2 illustrates the fingerprint of snoring in heart sound recordings displayed in the time domain.

FIG. 3 illustrates the fingerprint of snoring in heart sound recordings displayed in the time-frequency domain post-wavelet based filtering.

FIG. 5 illustrates the variation of the first and second heart sound amplitude with respiration.

DETAILED DESCRIPTION OF THE PREFERRED EMBODIMENTS

Figure 4:
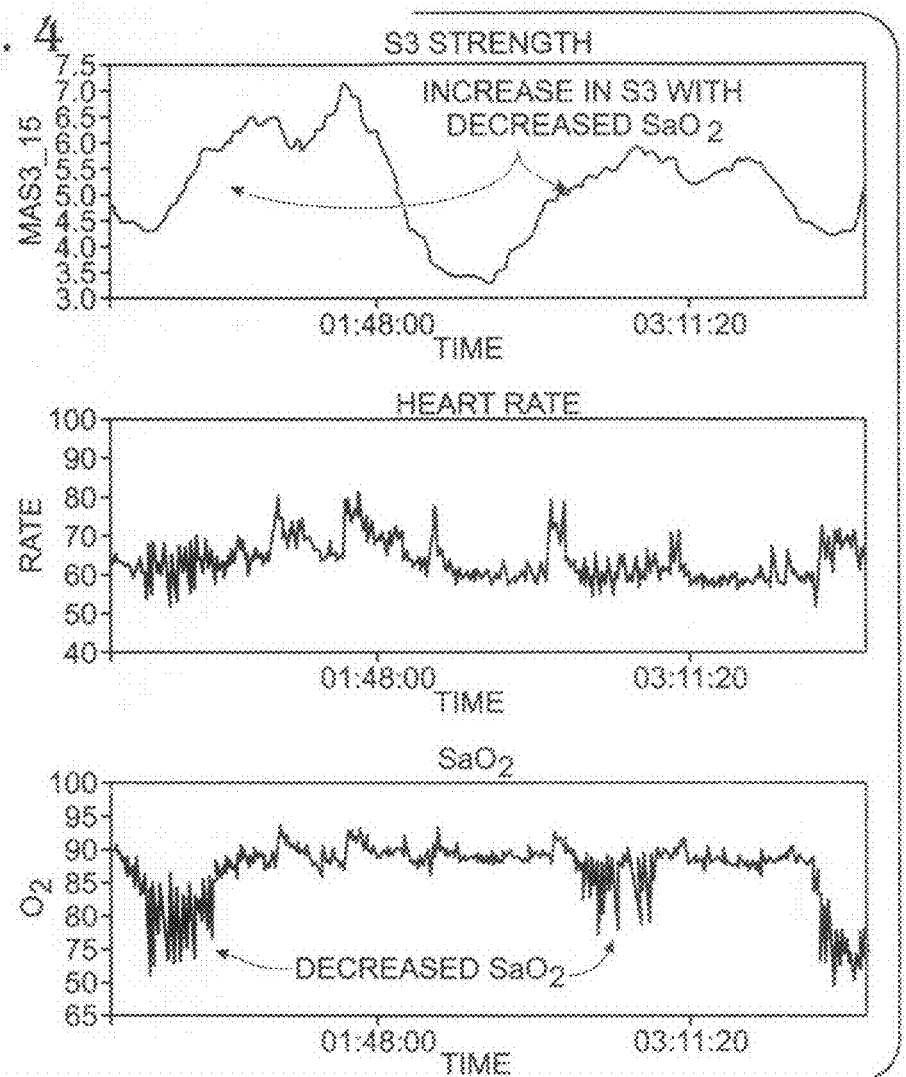
FIG. 4 illustrates a trend in S3 strength.

Episodes of snoring caused by central sleep apnea may be identified using continuous, computerized heart sound analysis. This is possible because snoring sounds are artifacts in the collection of heart sounds. Snoring sounds are discrete and non-predictable occurrence events. Referring now to FIG. 1, the method of the invention is depicted generally at 10. All relevant information may be obtained from a Holter device that collects ECG 12 and heart sounds 14. Heart sounds are collected in a bandwidth above 10 Hz and below 125 Hz. Such a collection device, and the limitation of the collection to ECG and heart sounds is significantly simpler than the devices used in a sleep laboratory, and facilitates patient monitoring in a non-laboratory setting, such as the patient's home environment, rather than requiring the patient to spend time in a sleep lab. The ECG and heart sound information is computer processed, 16, which processing includes wavelet transformation. The processed information analysis includes an analysis of whether snoring occurred (yes or no) 18; an analysis of the S1 heart sound variation over time 20; and a hemodynamic assessment, including analysis of S3 heart sound 22, also referred to herein as a "fingerprint". The latter assessment is more fully described in U.S. Pat. No. 7,174,203 B2, granted Feb. 6, 2007 to Arand et al., for *Method and System Relating to Monitoring and Characterization a Heart Condition*, and U.S. patent application Ser. No. 11/704,403, filed Feb. 8, 2007 by Nelson, for *Wavelet Transform and Pattern Recognition Method for Heart Sound Analysis*, both of which fully are incorporated herein by reference.

Heart sound S1 is indicative of respiration rate, and heart sound information distinguishes the severity of an apneic event, although nothing about the character of the event, e.g., central or obstructive. The analysis of S1 includes analysis of Q wave onset from the ECG to determine the start of electrical heart beat activity; and, to peak of the S1 to determine the mechanical response: a "short" response indicates efficient heart operation; a "long" response indicates a problem, which may be that breathing has stopped, i.e. an apneic event.

The hemodynamic assessment of heart sound S3 relates to the heart pump function. A rise in S3 strength, or intensity, indicates a weakened pump function, which may be the result of oxygen diminution in the heart. The trend 24 of the S3 strength analysis is indicative of oxygen content in the heart, and a lowering oxygen content may lead to an increase in the likelihood of an undesirable cardiac event. An S4 strength trend could also be employed to indicated reduced compliance of the heart due to ischemia, or reduced oxygen in the heart muscle.

Once the parameters have been analyzed, they are evaluated 26 and a treatment is applied 28 to the patient.

Part of the analysis and treatment protocol includes analyzing ECG and heart sound data as gathered by ECG sensors and heart sound sensors. Referring now to FIG. 2, which illustrates the variation of the first and second heart sound amplitude with respiration, in the lower graph 30, a trace of an ECG sensor 32 and a heart sound sensor 34 are depicted. The upper graph 36 depicts heart sounds S1 and S2 and a snoring event 38, and represents a hemodynamic assessment fingerprint. A snoring event is depicted in lower graph 30 at 40. Breathing pauses, which may be detected by detecting air flow, nasal or oral, or heart sound properties, i.e., the intensity and width of systolic heart sounds, e.g., first and second heart sounds. The presence and frequency of snoring may be identified through the combination of wavelet-based filtering of the heart sound signal and time-frequency analysis of the continuously filtered sound signal. As shown in FIG. 2, snoring manifests itself with a very specific "fingerprint" and can easily be separated from heart sounds, murmurs and other types of heart/lung sounds and external artifacts.

FIG. 3 illustrates the fingerprint of snoring in heart sound recordings displayed in the time domain and in the time-frequency domain post wavelet based filtering, while a snoring event is clearly present, the figure may or may not represent an apneic event.

FIG. 4 depicts a trend correlation between S3 strength, heart rate and SaO2 over time. Focusing attention particularly on S3 and SaO2, as SaO2 decreases, S3 strength, or intensity, increases. It is believed that the illustrated increases in S3 strength are the result of untreated sleep apneic events. Thus, a trend in the increase of S3 strength may be used to evaluate the presence of an apneic event.

During or after the acquisition of the data, a clinician may review the trends and the waveforms to determine the presence and extent of apneic events. The apneic events are typically associated with increases in heart rate, ischemic episodes and periods of arrhythmias. The clinician can use the ECG waveform itself as well as trends from the ECG data to ascertain the presence and severity of these changes due to apnea. In addition, since the apneic events can be associated with true hemodynamic changes, the clinician can use the S3 and S4 strength to determine if the ECG changes also coincide with reduced left ventricular contractility or decreased compliance of the heart due to ischemia. The S1 and/or S2 intensity and their associated trends can be used to determine respiratory cycles, respiratory rates and periods of apnea. A clinician will be empowered to make a diagnosis of sleep apnea when presented with these multiple sources of evidence of apnea (increased heart rate, ischemic ECG changes, arrhythmia, increased S3/S4 strength, and respiration rate from S1/S2).

Snoring may occur without the occurrence of an apneic event. The method of the invention establishes (1) the occurrence of an apneic event, as a result of the hemodynamic assessment; (2) that snoring has occurred; and (3) whether only snoring, without an apneic event, has occurred.

Figure 6:
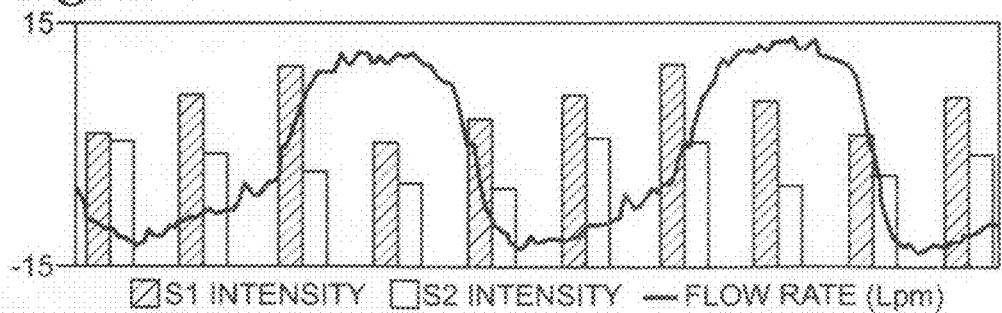
FIG. 6 depicts S1 and S2 intensity in conjunction with air flow rate.

FIGS. 5 and 6 depict normal ECG/heart sound traces/graphs where an apneic event is not present.

Thus, a method of snoring detection for differential sleep apnea diagnosis has been disclosed. It will be appreciated that further variations and modifications thereof may be made within the scope of the invention as defined in the appended claims.

We claim:

1. A computer-based detection and data-processing method employable with a sleeping subject for aiding in the differential-character assessment of apneic events comprising using a data-collection device attached to a sleeping subject, gathering simultaneously from that subject both (a) heart-sound, and related and included snoring-episode data, and (b) ECG data, relevant specifically to differential apneic detection, supplying the collected data to a computer for processing, performing in the computer, with respect to the gathered and supplied heart-sound, and related and included snoring-episode, data, time-frequency-intensity (TFI) analysis and wavelet-based filtering, and based on said performing, computer-producing time-based graphical output information which, on a common time-base in relation to ECG-waveform information, is indicative (a) of the presence and differential character of any gathered-data-detected apneic event, (b) whether snoring has occurred, and (c) whether only snoring, without an apneic event, has occurred.

2. The method of claim 1, wherein said computer-producing further includes creating a graphical output indication which is specifically indicative of snoring.

3. The method of claim 1, wherein said wavelet-based filtering includes computer-generating a time-frequency-intensity scalogram.

* * * * *